United States Patent [19]

Ziegler et al.

[11] 4,154,741

[45] May 15, 1979

[54] PROCESS FOR THE MANUFACTURE OF PYRONO-CONDENSED COUMARINS

[75] Inventors: Erich Ziegler; Otto Wolfbeis, both of Graz, Austria

[73] Assignee: Ciba-Geigy Corporation, Ardsley, N.Y.

[21] Appl. No.: 864,360

[22] Filed: Dec. 27, 1977

Related U.S. Application Data

[63] Continuation-in-part of Ser. No. 734,783, Oct. 22, 1976, abandoned.

[30] Foreign Application Priority Data

Nov. 3, 1975 [CH] Switzerland ...................... 14156/75

[51] Int. Cl.$^2$ ............................................ C07D 493/04
[52] U.S. Cl. ......................... 260/343.21; 260/343.42; 542/420
[58] Field of Search ............ 260/343.2, 343.21, 343.42

[56] References Cited

PUBLICATIONS

Checchi et al. "Chem. Abst." 67:64262(c) 1965.
March "Advanced Org Chem" (1968) pp. 464-465.
Nair, 74:111,944(h) (1971).
Ziegler et al., 73:45,383(a) (1970).
Anker et al., 76:59492j (1971).

*Primary Examiner*—Donald G. Daus
*Assistant Examiner*—David E. Wheeler
*Attorney, Agent, or Firm*—Prabodh I. Almaula

[57] ABSTRACT

A new process for the manufacture of pyrono-condensed coumarin compounds by reacting an anil derivative of a heterocyclic compound with a cyanoacetic acid derivative in the presence of a base and a strong polar aprotic solvent is described.

4 Claims, No Drawings

PROCESS FOR THE MANUFACTURE OF PYRONO-CONDENSED COUMARINS

This is a continuation-in-part of our copending application Ser. No. 734,783, filed Oct. 22, 1976, now abandoned.

The present invention provides a novel process for the manufacture of pyrono-condensed coumarin compounds.

It is known from Gazz. chim. ital. 95, 895 and 1502 (1956) to obtain pyrono-condensed coumarins by condensing 3-formyl-4-hydroxy-coumarin with diethyl malonate or with a cyanoacetic ester in anhydrous piperidine.

The invention is based on the surprising observation that pyrono-condensed coumarin compounds can be obtained by using as starting materials the Schiff's bases derived from 2-keto-3-formyl-4-hydroxy-coumarin compounds and aniline.

The process of the present invention for obtaining pyrono-condensed coumarin compounds of the formula

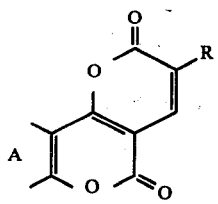

(1)

wherein

A represents an unsubstituted or substituted, mono- or dinuclear aromatic radical which is fused in the position indicated by the valence dashes, and R represents a cyano group, —CON(CH$_2$CH=CH$_2$)$_2$ or —COOY, wherein Y represents a hydrogen atom, a salt-forming cation, an alkyl group of 1 to 4 carbon atoms or an allyl group, comprises reacting a compound of the formula

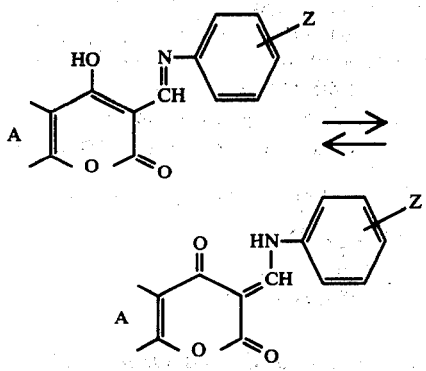

(2a)

(2b)

wherein

Z represents a hydrogen or chlorine atom, and

A is as defined in formula (1), in the presence of a base and of a strong polar aprotic solvent, at temperatures between 20° C. and the boiling point of the solvent, during 5 to 15 minutes, with a cyano derivative of the formula

NC—CH$_2$—R (3)

wherein R represents a cyano group, —CON(CH$_2$—CH=CH$_2$)$_2$ or —COOY, in which Y represents a hydrogen atom, a salt-forming cation, an alkyl group of 1 to 4 carbon atoms or an allyl group.

Fused aromatic radicals A are to be understood as meaning carbocyclic-aromatic fused mono- or dinuclear radicals.

Suitable substituents of the radicals A are: halogen atoms, alkyl groups of 1 to 12, preferably 1 to 4, carbon atoms, alkoxy groups of 1 to 12, preferably 1 to 4, carbon atoms, alkylamino groups of 1 to 12, preferably 1 to 4, carbon atoms, and hydroxyl groups.

Suitable bases are inorganic and organic compounds, for example those of lithium, sodium, potassium, rubidium, caesium, or ammonium, or secondary amines, such as piperidine or morpholine, and triethylamine. Preferred bases are sodium or potassium compounds of the formula

QOC$_{m-1}$H$_{2m-1}$ (4)

wherein

Q represents sodium or potassium and m is an integer from 1 to 6, preferably from 2 to 6, for example sodium or potassium hydroxide or sodium or potassium alcoholates.

Suitable strong polar aprotic solvents are primarily neutral to alkaline organic solvents which do not contain any atoms, in particular hydrogen atoms, which can be replaced by alkali metals, for example dialkyl amides of formic acid, acetic acid, and phosphoric acid, and tetraalkylureas, wherein alkyl represents an alkyl group containing 1 to 4 carbon atoms, in particular the methyl group.

As primary examples of such solvents there may be mentioned: diethyl formamide, hexamethyl-phosphoric triamide, tetramethyl urea, and, in particular, dimethyl formamide. These solvents can be used singly or mixed with other solvents, for example alcohols.

Within the scope of the present invention a preferred process is that for the manufacture of pyrono-condensed coumarin compounds of the formula

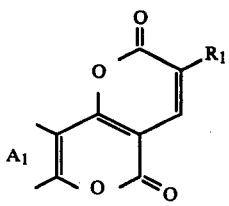

(5)

wherein

A$_1$ represents a 1,2-naphtho or benzo group, and

R$_1$ represents —CON(CH$_2$—CH=CH$_2$)$_2$ or —COOY, in which Y represents a hydrogen atom, a salt-forming cation, an alkyl group of 1 to 4 carbon atoms or an allyl group, which process comprises reacting a compound of the formula

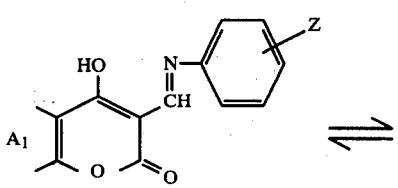

(6a)

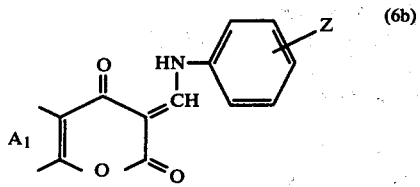
(6b)

wherein $A_1$ and $Z$ are as previously defined, with a cyano derivative of the formula $$NC-CH_2-R_1 \qquad (7)$$

wherein $R_1$ is as defined in formula (5).

A particularly preferred process is that for the manufacture of pyrono-condensed coumarins of the formula

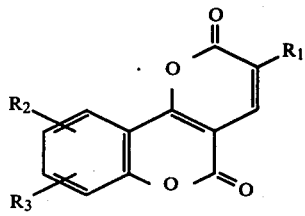
(8)

wherein
$R_1$ is as defined in formula (5),
$R_2$ represents a hydrogen atom, a hydroxyl group, an alkyl group of 1 to 4 carbon atoms, an alkoxy group of 1 to 4 carbon atoms or an alkylamino group containing 1 to 4 carbon atoms in the alkyl moiety, and
$R_3$ represents a hydrogen atom, a hydroxyl group, an alkyl group of 1 to 4 carbon atoms, whilst $R_2$ and $R_3$ in ortho-position to each other also represent the 1,3-butadienylene group,
and of those of the formula

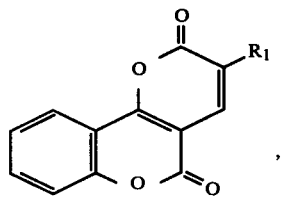
(9)

wherein
$R_1$ is as defined in formula (5), which process comprises reacting a compound of the formula

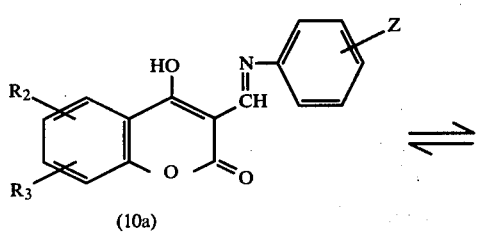
(10a)

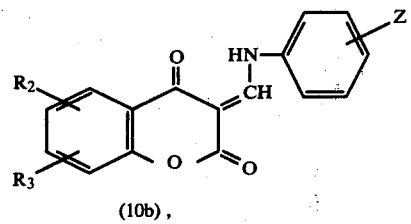
(10b), or

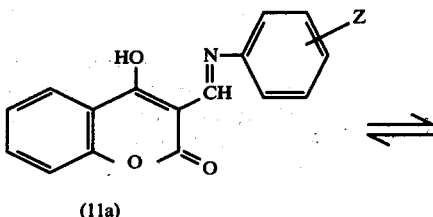
(11a)

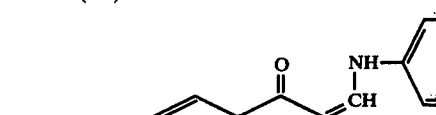
(11b), wherein
$Z$, $R_2$ and $R_3$ are as previously defined above, with a cyano derivative of the formula $$NC-CH_2-R_1 \qquad (7),$$

wherein $R_1$ is as defined in formula (5).

The compounds which can be obtained according to the invention are known [S. Checci, G. Auzzi, Gazz. chim. ital. 95, 985 and 1502 (1965)]. They possess fluorescent properties and can be used as fluorescent dyes and, depending on the substitution, as laser dyes [App. Phys. Lett. 16, 405 (1970); 17, 189 (1970) and J. Am. Chem. Soc. 96, 9699 (1974)].

The starting materials of the formulae (2a), (2b), (10a), (10b), (11a) and (11b) are partly new and partly known. The new starting materials are obtained by reacting in known manner a compound of the formula

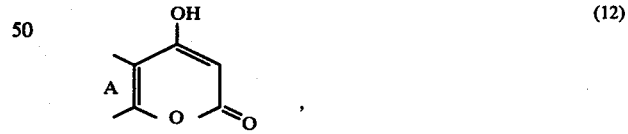
(12)

wherein A is as defined above, with substituted or unsubstituted aniline and ethyl orthoformate [CH(OC$_2$H$_5$)$_3$].

The following Examples will serve to illustrate the invention in more detail but imply no limitation to what is described therein.

EXAMPLE 1

3 g (16.8 mmoles) of 4,7-dihydroxy-coumarin are dissolved in 25 ml of hot glacial acetic acid. To this solution is added a mixture of 1.6 g (17.7 mmoles) of aniline and 3 ml of triethyl orthoformate and the batch is refluxed for 10 minutes. After the reaction mixture has cooled, 4.3 g (84% of theory) of the anil (Schiff's base) of the formula

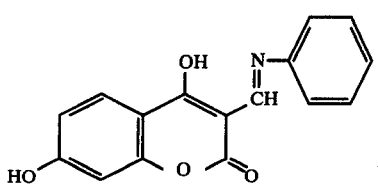
(101)

are obtained as yellowish crystals with a melting point of 322°-324° C.

This anil (0.1 g) and 0.6 g of ethyl cyanoacetate are dissolved warm in 10 ml of dimethyl formamide. The solution is heated to 80°-90° C. and treated with a solution of 0.8 g of potassium hydroxide in 5 ml of absolute ethanol. The mixture is kept for a further 10 minutes at this temperature and diluted with 50 ml of water.

The aqueous solution is adjusted to a pH value of 1 with hydrochloric acid and then neutralised with solid sodium bicarbonate. After 3 hours the precipitated product is collected by suction filtration and dried at 80° C. Recrystallisation from glacial acetic acid yields 0.65 g (69% of theory) of the compound of the formula

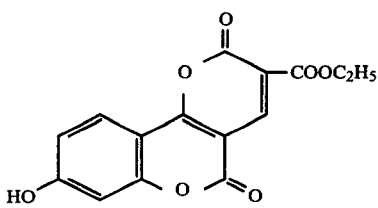
(102)

in the form of yellowish crystals with a melting point of 243°-245° C. (with decomp.).

Analysis: $C_{15}H_{10}O_7$ (302.3)

|  | C | H |
|---|---|---|
| calculated: | 59.61 | 3.33 |
| found: | 59.44 | 3.39 |

If the above procedure is repeated using methyl cyanoacetate instead of ethyl cyanoacetate, then recrystallisation from glacial acetic acid yields the compound of the formula

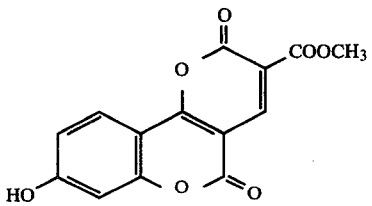
(103)

in the form of yellowish crystals with a melting point of 288°-290° C. (with decomp.).

Analysis: $C_{14}H_8O_7$ (288.2)

|  | C | H |
|---|---|---|
| calculated: | 58.34 | 2.80 |
| found: | 58.54 | 2.98 |

EXAMPLE 2

3 g of 4-hydroxy-coumarin are dissolved warm in 25 ml of glacial acetic acid. To this solution is added a mixture of 1.6 g of aniline and 3 ml of triethyl orthoformate and the batch is refluxed for 10 minutes. The reaction mixture is allowed to cool and the precipitate which has formed is filtered off after 5 hours. Yield: 4.47 g (91% of theory) of the compound of the formula

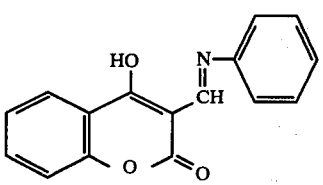
(104)

in the form of light yellow crystals with a melting point of 208° C. (from dimethyl formamide).

This product (4 g) is dissolved in 50 ml of hot dimethyl formamide and 6 g of ethyl cyanoacetate are added to the solution. The solution is heated to 100° C. and treated with a solution of 2 g of potassium hydroxide in 10 ml of anhydrous ethanol. The reaction mixture is cooled to 80° C. and kept at this temperature for 5 minutes. The still warm reaction mixture is poured onto 10 times its volume of ice-water, acidified with concentrated hydrochloric acid, and neutralised with sodium bicarbonate solution. After 3 hours the precipitate which has formed is collected by suction filtration, digested with water, and dried in a drying cabinet. Recrystallisation from glacial acetic acid yields 2.22 g (66% of theory) of the compound of the formula

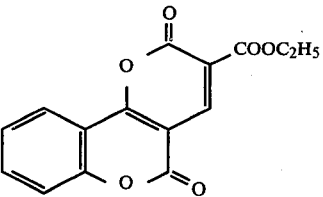
(105)

in the form of colourless crystals with a melting point of 202° C.

Analysis: $C_{15}H_{10}O_6$ (286.3)

|  | C | H |
|---|---|---|
| calculated: | 62.94 | 3.52 |
| found: | 62.89 | 3.52. |

By repeating the procedure as described in Examples 1 and 2, but using the starting materials listed in columns A and B of Table 1, the end products indicated in column C are obtained.

TABLE I

| Compound | A<br>Cyano compound | B<br>Anil | C<br>End product | m.p.<br>in °C. |
|---|---|---|---|---|
| 106 | CN—CH$_2$—COOCH | | | 225 |
| 107 | CN—CH$_2$—COOC$_2$H$_5$ | | | 195 |
| 108 | CN—CH$_2$—COOC$_2$H$_5$ | | | 276 |
| 109 | CN—CH$_2$—COOC$_2$H$_5$ | | | 228 |
| 110 | CN—CH$_2$—COOC$_2$H$_5$ | | | |
| 111 | CH—CH$_2$—COOCH$_2$CH=CH$_2$ | | | 181 |
| 112 | CN—CH$_2$CON(CH$_2$CH=CH$_2$)$_2$ | | | 243 |

We claim:

1. A process for the manufacture of pyrono-condensed coumarin compounds of the formula

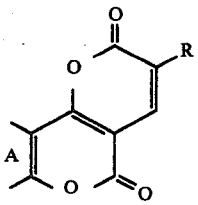

wherein
- A represents an unsubstituted or substituted 1,2-naphtho or benzo group which is fused in the position indicated by the valence dashes, and the substituents are selected from the group consisting of halo, alkyl of 1 to 12, alkoxy having 1 to 12 carbon atoms, alkylamino having 1 to 12 carbon atoms and hydroxyl, and
- R represents a cyano group, —CON(CH$_2$CH=CH$_2$)$_2$ or —COOY, wherein Y represents a hydrogen atom, a salt-forming cation, an alkyl group of 1 to 4 carbon atoms or an allyl group, which process comprises the step of reacting a compound of the formula

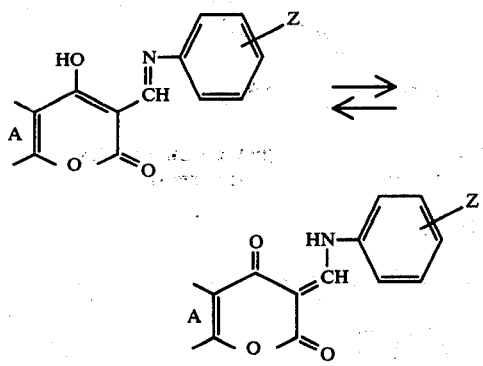

wherein
Z represents a hydrogen or chlorine atom, and
A is as defined above,
in the presence of a base and a strong polar, aprotic solvent, at temperatures between 20° C. and the boiling point of the solvent, during 5 to 15 minutes, with a substituted acetonitrile of the formula

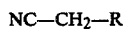

wherein R represents a cyano group, —CON(CH$_2$CH=CH$_2$)$_2$ or —COOY, wherein Y represents a hydrogen atom, a salt-forming cation, an alkyl group of 1 to 4 carbon atoms or an allyl group.

2. A process according to claim 1 for the manufacture of pyrono-condensed coumarin compounds of the formula

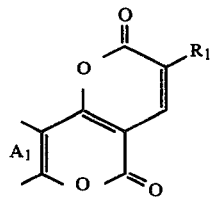

wherein
A$_1$ represents a 1,2-naphtho or benzo group, and
R$_1$ represents —CON(CH$_2$—CH=CH$_2$)$_2$ or —COOY, wherein Y represents a hydrogen atom, a salt-forming cation, an alkyl group of 1 to 4 carbon atoms or an allyl group, which process comprises the step of reacting a compound of the formula

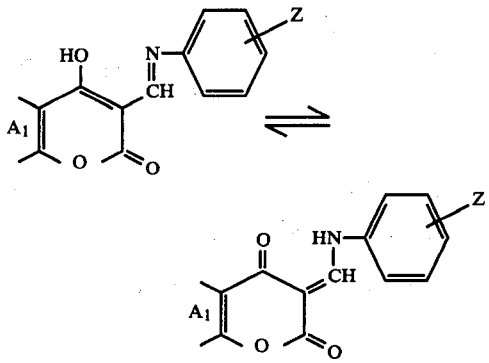

wherein
Z represents a hydrogen or chlorine atom, and
A$_1$ is as defined above,
with a substituted acetonitrile of the formula

wherein R$_1$ represents —CON(CH$_2$CH=CH$_2$)$_2$ or —COOY, in which Y represents a hydrogen atom, a salt-forming cation, an alkyl group of 1 to 4 carbon atoms or an allyl group.

3. A process according to claim 2 for the manufacture of pyrono-condensed coumarin compounds of the formula

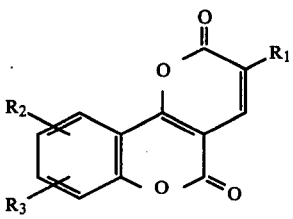

wherein
R$_1$ is as defined in claim 2,
R$_2$ represents a hydrogen atom, a hydroxyl group, an alkyl group of 1 to 4 carbon atoms, an alkoxy group of 1 to 4 carbon atoms or an alkylamino group of 1 to 4 carbon atoms in the alkyl moiety, and
R$_3$ represents a hydrogen atom, a hydroxyl group, an alkyl group of 1 to 4 carbon atoms or an alkoxy group of 1 to 4 carbon atoms, whilst R$_2$ and R$_3$ in ortho-position to each other also represent the 1,3-butadienylene group, which process comprises the step of reacting a compound of the formula

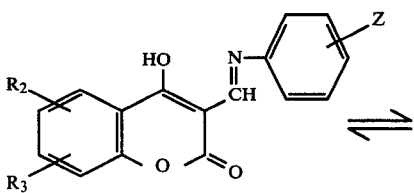

-continued

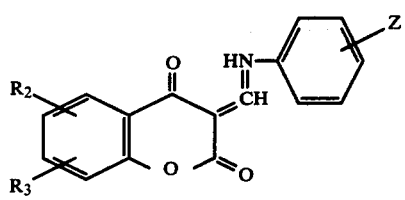

wherein

Z represents a hydrogen or chlorine atom and

R₂ and R₃ are as defined above, with a substituted acetonitrile of the formula

NC—CH₂—R₁, wherein R₁ represents —CON(CH₂CH=CH₂)₂ or —COOY, in which Y represents a hydrogen atom, a salt-forming cation, an alkyl group of 1 to 4 carbon atoms or an allyl group.

4. A process according to claim 3 for the manufacture of pyrono-condensed coumarin compounds of the formula

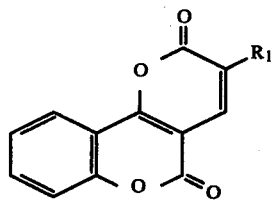

wherein R₁ represents —CON(CH₂CH=CH₂)₂ or —COOY, in which Y represents a hydrogen atom, a salt-forming cation, an alkyl group of 1 to 4 carbon atoms or an allyl group, which process comprises the step of reacting a compound of the formula

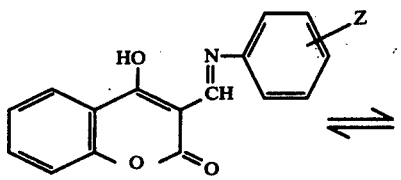

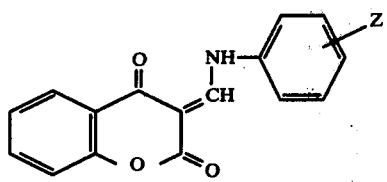

wherein Z represents a hydrogen or chlorine atom, with a substituted acetonitrile of the formula

NC—CH₂—R₁, wherein R₁ is as defined above.

* * * * *